United States Patent
Servedio et al.

(10) Patent No.: US 11,950,818 B2
(45) Date of Patent: Apr. 9, 2024

(54) IMPLANT CUTTER

(71) Applicant: Shukla Medical, St. Petersburg, FL (US)

(72) Inventors: Brian Joseph Servedio, St. Petersburg, FL (US); Zachary Robert Sweitzer, Keyport, NJ (US); Alexander Manning Jones, Savannah, GA (US)

(73) Assignee: Shukla Medical, St. Petersburg, FL (US)

( * ) Notice: Subject to any disclaimer, the term of this patent is extended or adjusted under 35 U.S.C. 154(b) by 832 days.

(21) Appl. No.: 17/032,151

(22) Filed: Sep. 25, 2020

(65) Prior Publication Data

US 2021/0093368 A1    Apr. 1, 2021

Related U.S. Application Data

(60) Provisional application No. 62/908,436, filed on Sep. 30, 2019.

(51) Int. Cl.
| | |
|---|---|
| *A61B 17/88* | (2006.01) |
| *A61B 17/70* | (2006.01) |
| *B23C 3/16* | (2006.01) |
| *A61B 17/00* | (2006.01) |

(52) U.S. Cl.
CPC ...... *A61B 17/8863* (2013.01); *A61B 17/7002* (2013.01); *B23C 3/16* (2013.01); *A61B 2017/00424* (2013.01); *A61B 2017/0046* (2013.01); *A61B 2017/00858* (2013.01)

(58) Field of Classification Search
CPC ..... A61B 17/88; A61B 17/8863; A61B 17/70; A61B 17/7002; B23C 3/16
See application file for complete search history.

(56) References Cited

U.S. PATENT DOCUMENTS

| | | | |
|---|---|---|---|
| 9,427,274 B1 | 8/2016 | McVean et al. | |
| 9,750,512 B2 * | 9/2017 | Jerke | A61B 17/1728 |
| 9,801,641 B2 * | 10/2017 | Keiser | A61B 17/17 |
| 10,327,787 B2 * | 6/2019 | Brotman | A61B 17/17 |
| 2014/0155905 A1 * | 6/2014 | Keiser | A61B 17/17 606/96 |
| 2017/0245907 A1 * | 8/2017 | Sharifi-Mehr | B23Q 11/0071 |

FOREIGN PATENT DOCUMENTS

EP    3210555 A1    8/2017

OTHER PUBLICATIONS

International Search Report for International Application No. PCT/US2021/033135, dated Sep. 15, 2021.
Written Opinion of the International Searching Authority for International Application No. PCT/US2021/033135, dated Sep. 15, 2021.

* cited by examiner

*Primary Examiner* — Christopher J Beccia
(74) *Attorney, Agent, or Firm* — Kim IP Law Group LLC

(57) ABSTRACT

A cutter for cutting an implant is provided. The cutter includes a handle; a handle coupler coupled to the handle; a drill guide coupled to the handle coupler and including at least one window; a mill extending through the handle coupler and the drill guide and disposed to rotate freely therein; and a catch cup circumscribing the drill guide to maintain chips of the implant removed by the mill.

20 Claims, 12 Drawing Sheets

IMPLANT CUTTER

CROSS REFERENCE TO RELATED APPLICATIONS

The present application claims the benefit of U.S. Provisional Patent Application No. 62/908,436 filed on Sep. 30, 2019 and entitled "Spine Rod Cutter," the entire disclosure of which is hereby incorporated herein by reference.

BACKGROUND OF THE INVENTION

Various types of surgeries involve the placement of implants, such as spine rods, within patients. There is often a need or desire to adjust the length of a spine rod after it has been implanted, as precise determination of the exact length of the spine rod can often be difficult or impossible to predict prior to surgery. Standard protocol for certain surgical procedures may also require cutting a spine rod after implantation to best provide an ideal, customized length for an individual patient. To adjust the length, the spine rod may be removed from the patient, cut to the desired length off-site and re-implanted within the patient at a later time. However, this procedure is time-consuming, costly, and requires patients to undergo multiple surgeries. There is, thus, a need for an efficient and effective implant cutter that may be employed in-situ to adjust the length of a spine rod or other implant.

BRIEF SUMMARY OF THE INVENTION

In accordance with an exemplary embodiment of the subject disclosure, a cutter for cutting an implant is provided. The cutter includes a handle; a handle coupler for coupling to the handle; a drill guide for coupling to the handle coupler and including at least one window; a mill for extending through the handle coupler and the drill guide and disposed to rotate freely therein; and a catch cup for circumscribing the drill guide to maintain chips of the implant removed by the mill.

In accordance with an aspect of the subject disclosure, the handle is hourglass shaped.

In accordance with another aspect of the subject disclosure, the handle is provided with at least one of stippling, texturing, and a slip-free coating.

In accordance with still another aspect of the subject disclosure, the handle coupler includes a central bore and the drill guide includes a proximal mating end structured to be received within the central bore of the handle coupler.

In accordance with yet another aspect of the subject disclosure, the handle coupler includes at least one first guide surface in communication with the central bore and the proximal mating end of the drill guide includes at least one second guide surface for engaging with the first guide surface of the handle coupler.

In accordance with still another aspect of the subject disclosure, the handle coupler includes a threaded screw bore and the handle includes a screw-like connector for engaging with the threaded screw bore to couple the handle to the handle coupler.

In accordance with yet another aspect of the subject disclosure, the drill guide includes a distal engaging end having a cutout shaped to engage with the implant.

In accordance with still another aspect of the subject disclosure, the drill guide includes a distal engaging end having a cutout shaped to engage with a spine rod.

In accordance with yet another aspect of the subject disclosure, the drill guide includes a mill receipt bore, an outside surface and at least one window extending from the mill receipt bore to the outside surface.

In accordance with still another aspect of the subject disclosure, the at least one window includes a top surface oriented substantially transversely to the transport receipt groove.

In accordance with yet another aspect of the subject disclosure, the at least one window includes a top surface oriented substantially parallelly to the transport receipt groove.

In accordance with still another aspect of the subject disclosure, the mill includes a milling bit extending distally to a cutting end and a helical transport groove extending proximally from the cutting end to a stop.

In accordance with yet another aspect of the subject disclosure, the cutting end is a flat cutting end with rounded edges.

In accordance with still another aspect of the subject disclosure, the handle coupler includes a proximal end surface and the mill includes a proximal connector having a distally facing stopping surface for engaging with the proximal end surface to prevent over-advancement of the mill distally into the drill guide.

In accordance with another exemplary embodiment of the subject disclosure, a cutter is provided. The cutter includes a handle; a handle coupler for coupling to the handle; a drill guide for coupling to the handle coupler and including at least one window; a mill for extending through the handle coupler and the drill guide and disposed to rotate freely therein; and a catch cup circumscribing the drill guide to maintain chips of the implant removed by the mill.

In accordance with still another exemplary embodiment of the subject disclosure, a cutter is provided. The cutter includes a handle coupler having an outside surface, proximal and distal end surfaces extending transversely to the outside surface, a central bore extending longitudinally from the proximal end surface to the distal end surface, and a threaded screw bore extending radially from the central bore to the outside surface of the handle coupler; a handle having a proximal gripping end and a distal connecting end having a screw-like connector, the screw-like connector engaging with the threaded screw bore and extending into the central bore of the handle coupler; a drill guide having an outside surface, a proximal mating end disposed within the central bore of the handle coupler and maintained therein by the screw-like connector of the handle, a distal engaging end having a cutout shaped to receive the implant, a longitudinally extending mill receipt bore extending from the mating end to the engaging end, a window extending radially from the mill receipt bore to the outside surface of the drill guide, and circumferential screw threads on the outside surface of the drill guide; a mill extending through the central bore of the handle coupler and into the mill receipt bore of the drill guide, the mill including a proximal connector having a distally facing stopping surface, a milling bit extending distally from the proximal connector to a distal cutting end, and a helical transport groove extending proximally from the distal cutting end to a stop; a catch cup circumscribing the drill guide, the catch cup including a proximal end abutting the distal end surface of the handle coupler, a distal end provided with inside threads engaging with the circumferential screw threads of the drill guide, and a longitudinal bore having a diameter greater than an outside diameter of the drill guide and extending from the inside threads to the proximal end of the catch cup; and a receiving cavity formed by the catch cup and drill guide.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

DETAILED DESCRIPTION OF THE INVENTION

Figure 1A:
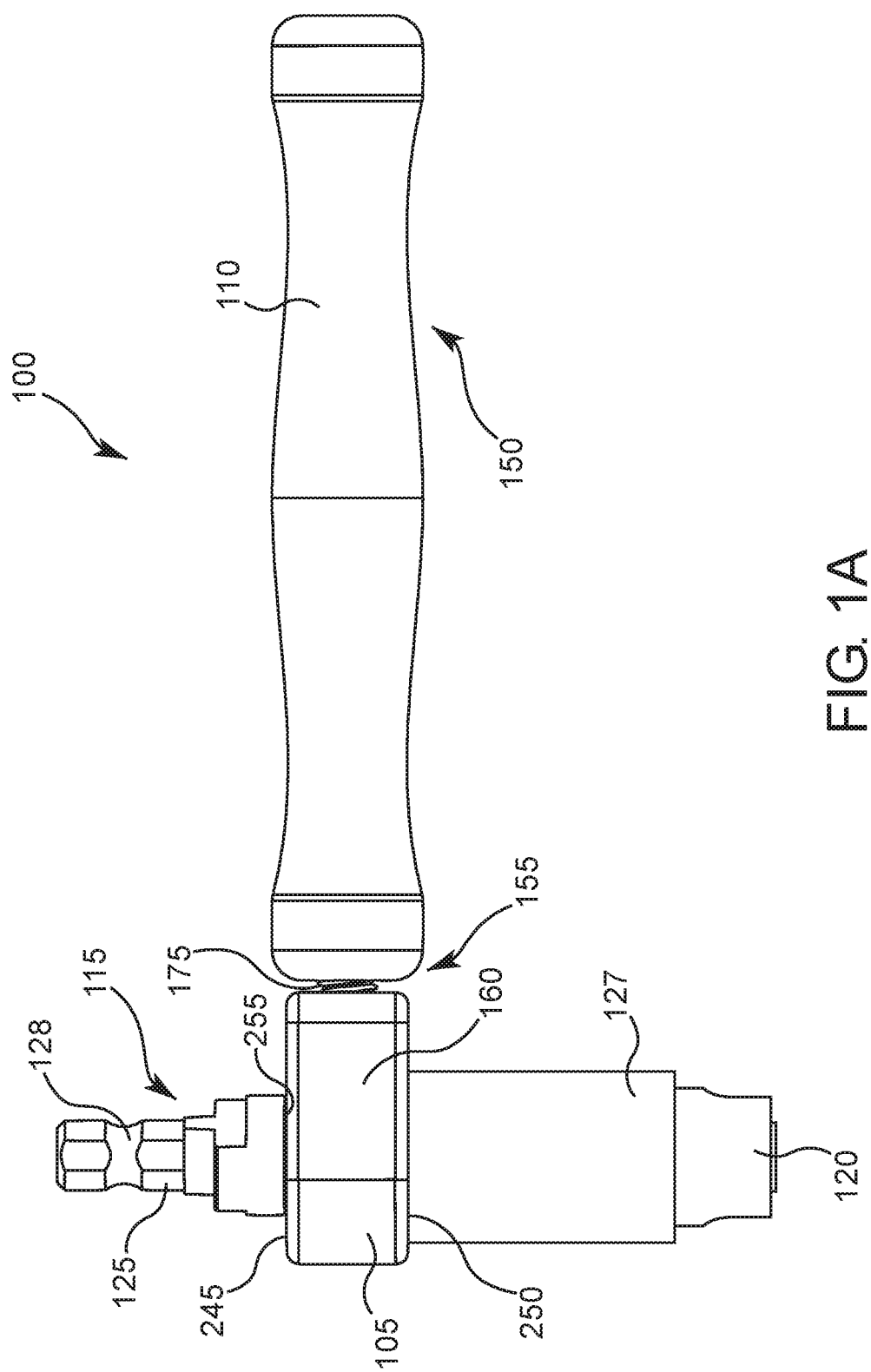
FIG. 1A is a side view of a cutter in accordance with an exemplary embodiment of the subject disclosure.

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

"Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more exemplary embodiments. One skilled in the relevant art will recognize, in light of the description herein, that the subject disclosure can be practiced without one or more of the specific features or advantages of a particular exemplary embodiment. In other instances, additional features and advantages may be recognized in certain exemplary embodiments that may not be present in all exemplary embodiments of the present disclosure.

Referring now to the Figures, there is seen an exemplary cutter 100 for cutting an implant, such as a spine rod 500 (see FIG. 1B), in accordance with the subject disclosure. Cutter 100 may be employed, for example, to cut implanted spine rods of varying lengths and diameters (e.g., 6 mm), and may be constructed from various materials, such as, for example, stainless steel, titanium, or cobalt chrome.

The cutter 100 includes a handle coupler 105, a handle 110 coupled transversely to the handle coupler 105, a mill 115 extending longitudinally through the handle coupler 105 and disposed to rotate freely therein, a drill guide 120 coupled to the handle coupler 105 and circumscribing the mill 115, and a catch cup 127 coupled to and circumscribing the drill guide 120 for maintaining chips and other fragments cut/milled from the implant by the mill 115.

As best shown in FIGS. 1A, 1B, 5A and 5B, the handle coupler 105 includes an outside surface 160, proximal and distal end surfaces 245, 250 extending transversely to the outside surface 160, a central bore 165 extending longitudinally from the proximal end surface 245 to the distal end surface 250, longitudinally extending and diametrically opposed guide surfaces 167, 167' in communication with the central bore 165, and a threaded screw bore 170 extending radially from the central bore 165 to the outside surface 160 about its posterior end.

Figure 1B:
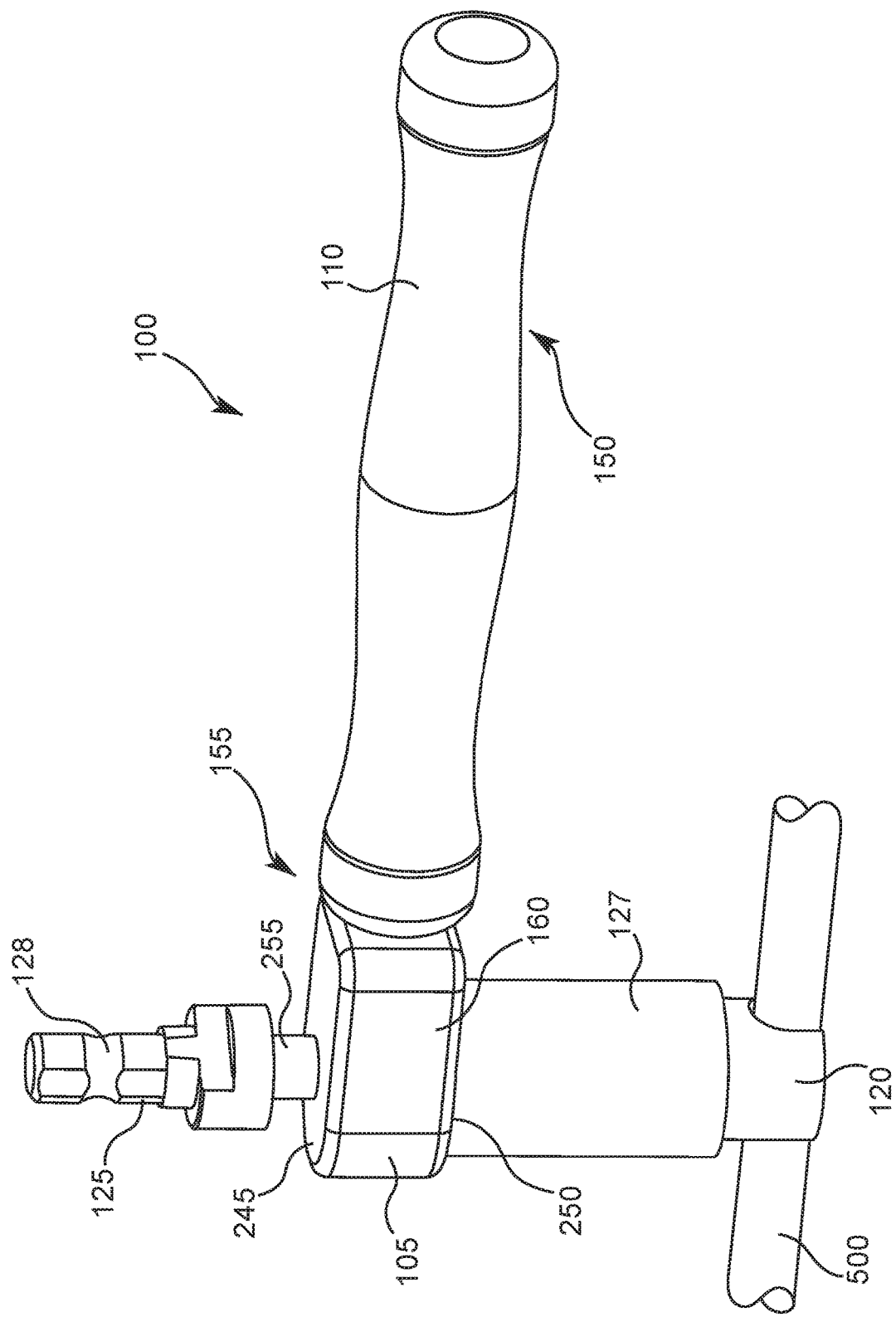
FIG. 1B is a perspective view of the cutter of FIG. 1A engaging a spine rod.
Figure 3:
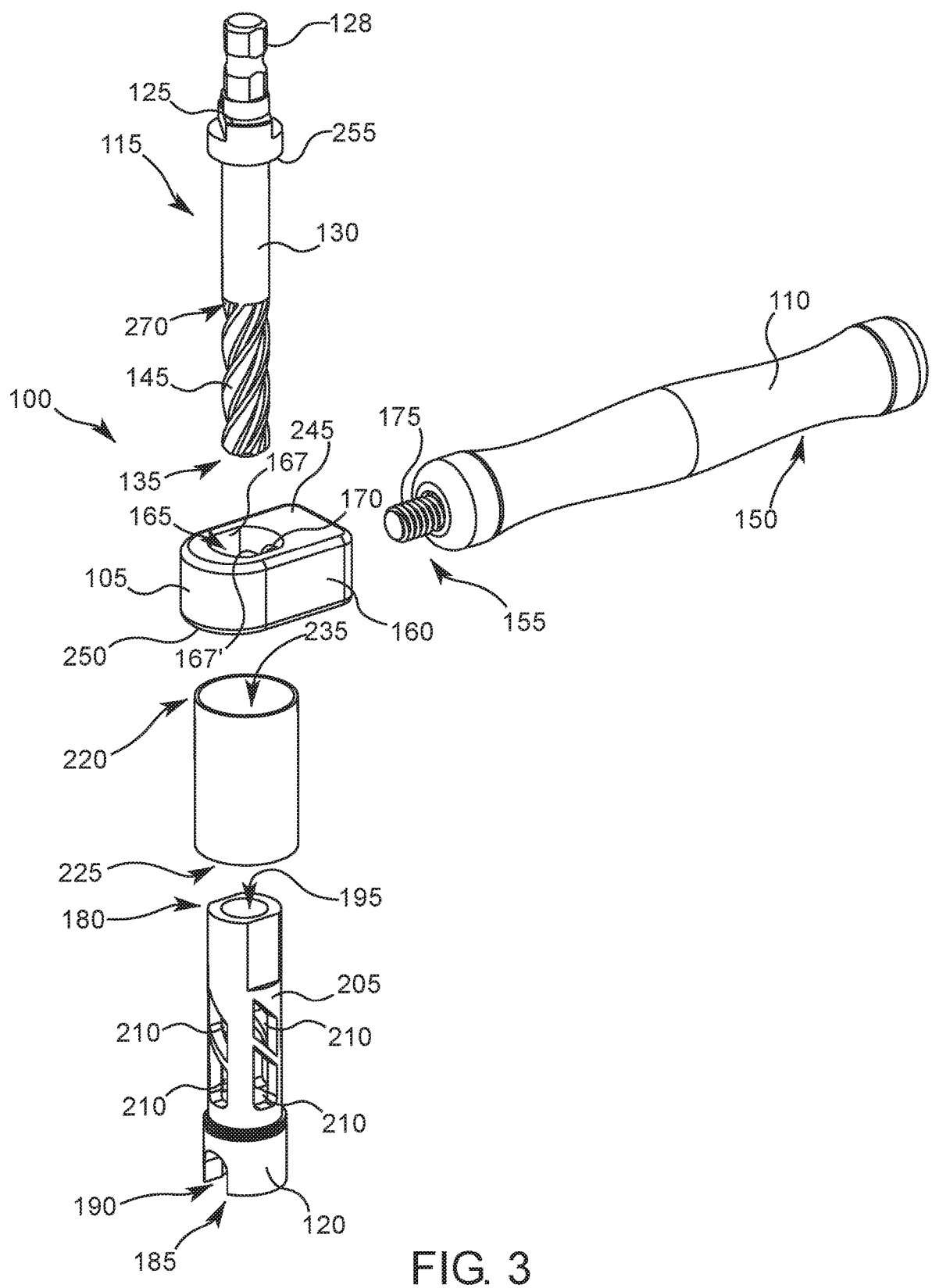
FIG. 3 is an exploded perspective view of the cutter of FIG. 1A.

As best shown in FIGS. 1A, 1B and 3, the handle 110 includes a proximal gripping end 150 and a distal connecting end 155 for coupling to the handle coupler 105. The proximal gripping end 150 may be constructed from any suitable materials, such as a metal, composite or polymer, and may be shaped to promote ergonomic gripping by a user. In the embodiment depicted in the Figures, for example, the gripping end 150 exhibits an hourglass-shape to promote easy gripping, though it should be appreciated that the gripping end 150 may exhibit other shapes and include other structures and/or features to promote gripping. For example, the gripping end 150 may include concave indents for receiving the user's fingers and/or be provided with texturing (e.g., knurling), stippling, and/or slip-free coatings (such as flexible polymers, rubbers, etc.) to increase friction between the gripping end 150 and the user's hands.

The distal connecting end 155 of the handle 110 is structured to couple to the handle coupler 105. In the embodiment depicted in the Figures, the distal connecting end 155 includes a screw-like connector 175 for engaging with the threaded screw bore 170 of the handle coupler 105, though it should be appreciated that the distal connecting end 155 and/or the handle coupler 105 may be provided with other structures for coupling the handle 110 to the handle coupler 105, and that various embodiments of the subject disclosure are not intended to be limited to any particular structure(s) for doing so.

Figure 4A:
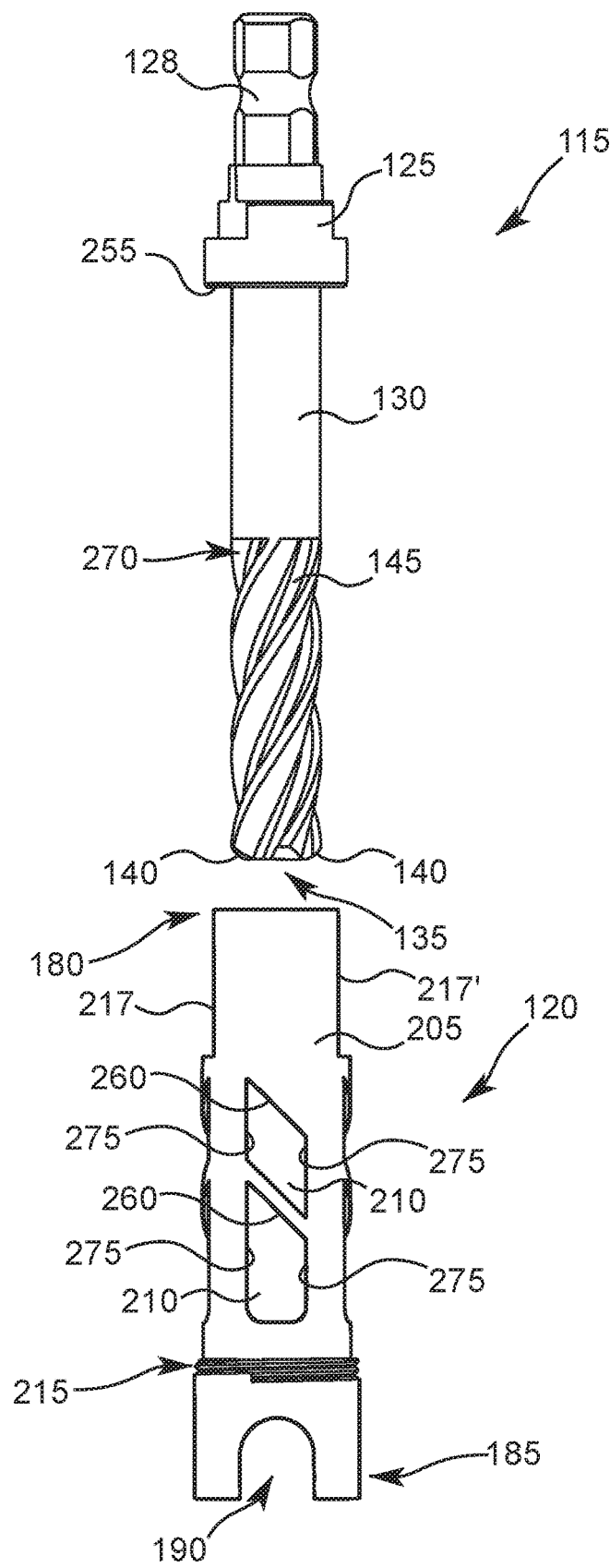
FIG. 4A is a front elevation view of a mill and drill guide of the cutter of FIG. 1A.
Figure 4B:
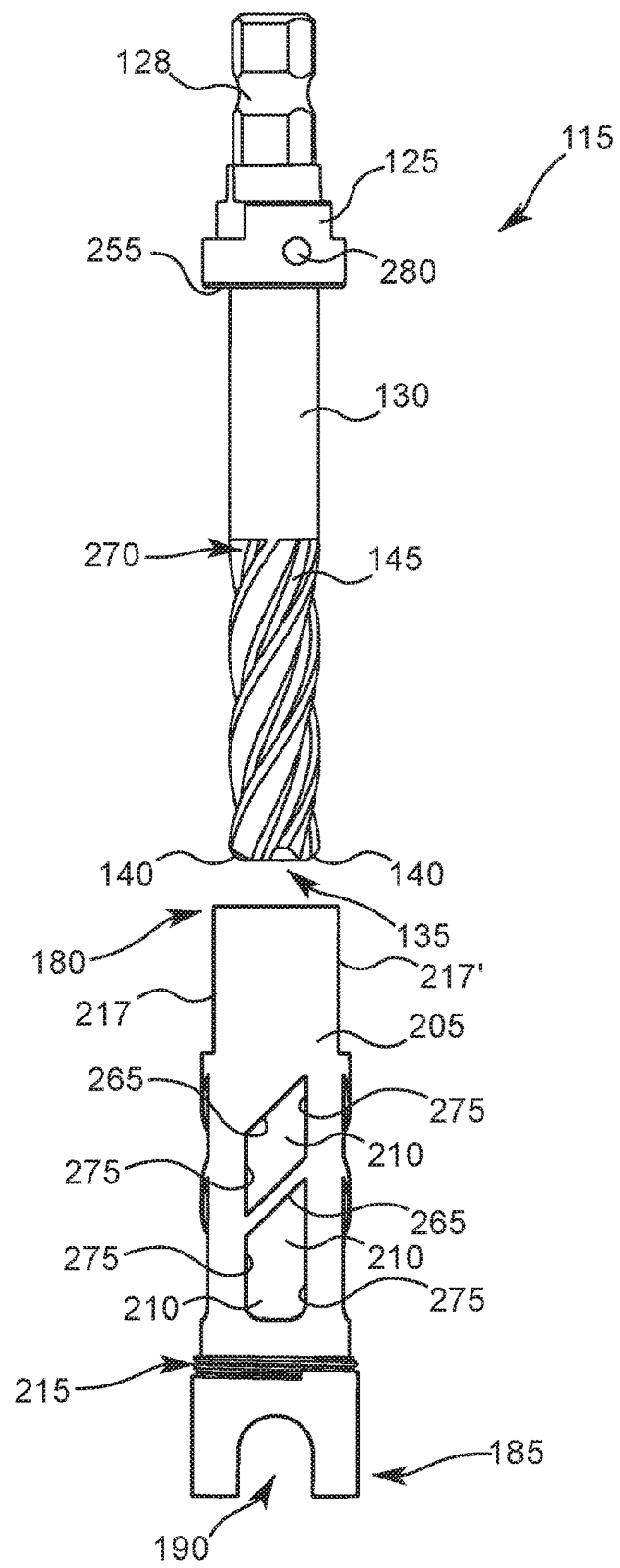
FIG. 4B is a rear elevation view of the mill and drill guide of FIG. 4A.
Figure 5A:
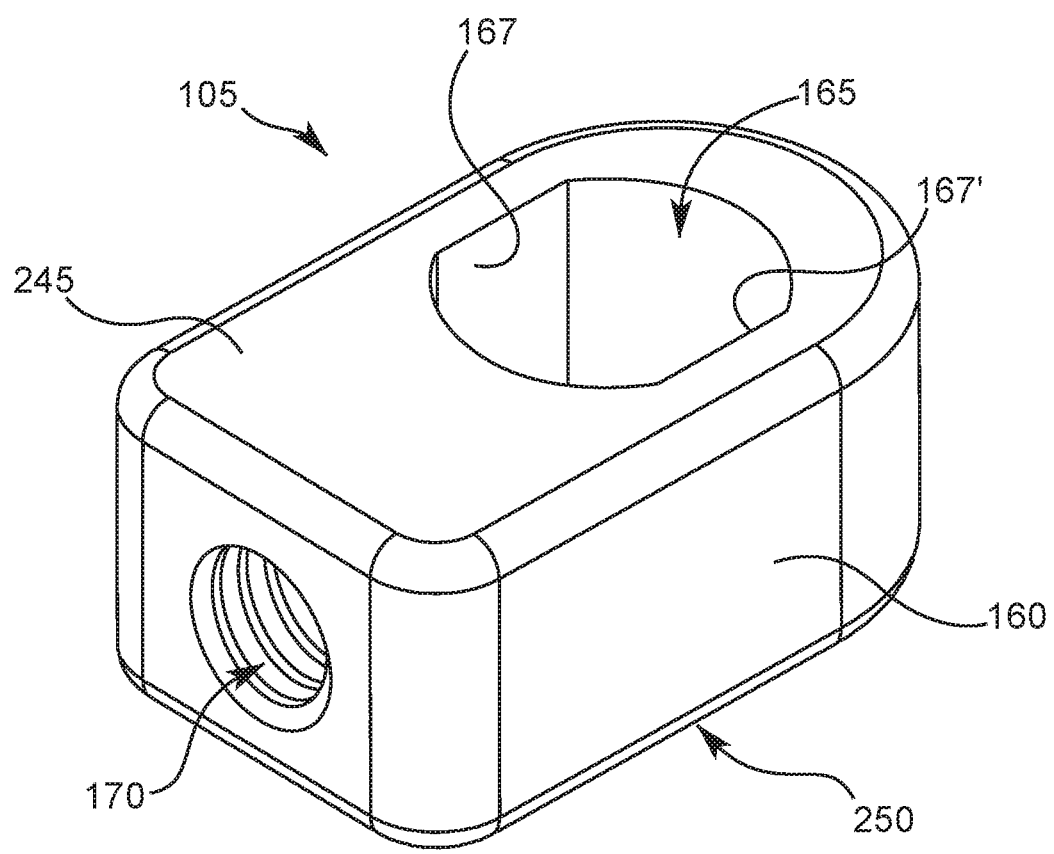
FIG. 5A is a perspective view of a handle coupler of the cutter of FIG. 1A.
Figure 5B:
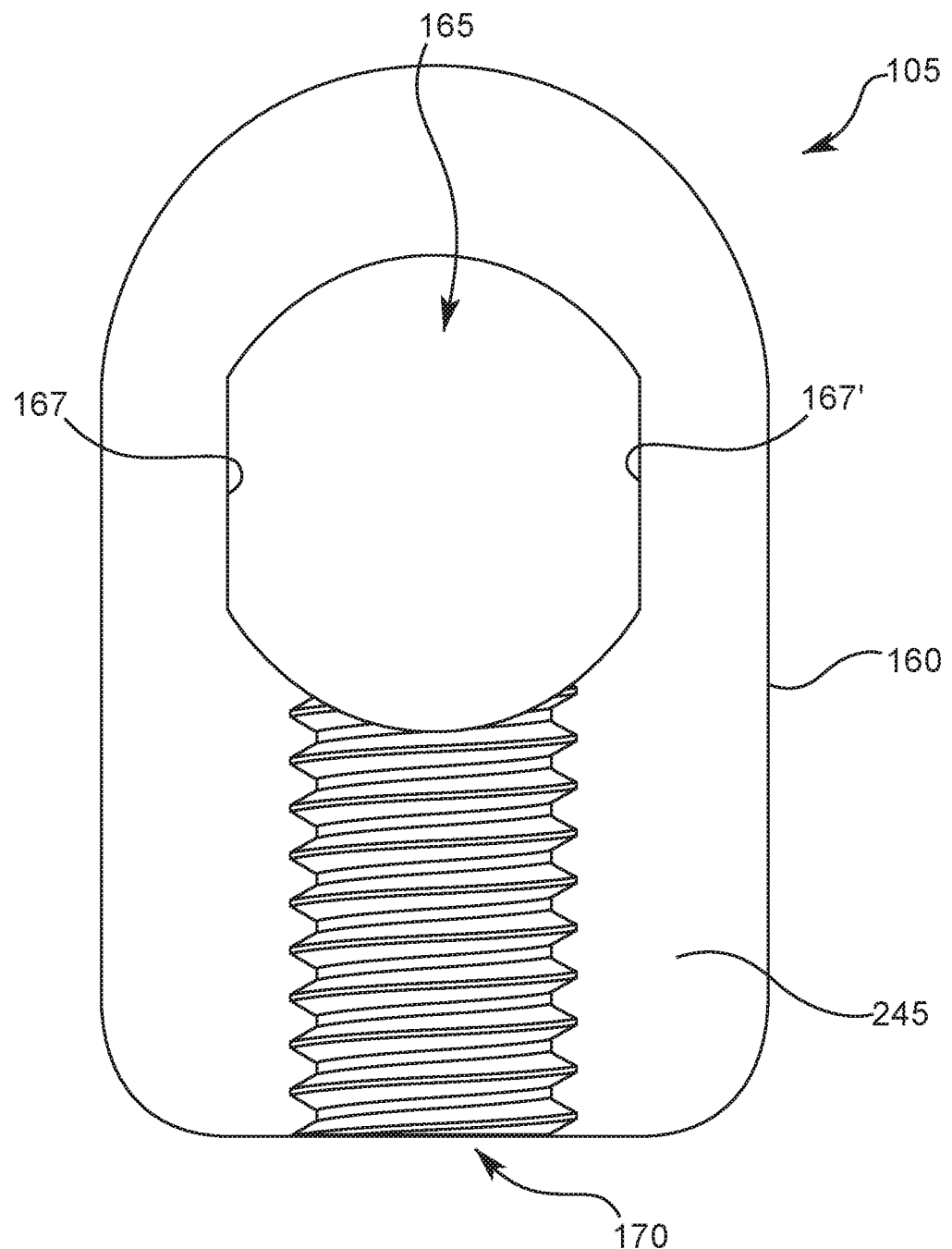
FIG. 5B is a cross-sectional view of the handle coupler of FIG. 5A.

As best shown in FIGS. 3, 4A and 4B, the mill 115 includes a proximal connector 125, a cylindrically-shaped milling bit 130 extending distally from the proximal connector 125 to a distal cutting end 135 which may include rounded edges 140, and a helical transport groove 145 extending proximally from the distal cutting end 135 to a stop 270 on the outside surface of the milling bit 130, though it should be appreciated that the milling bit 130 may be shaped differently and include other structures suitable for cutting/milling medical implants, and that various embodiments of the subject disclosure are not intended to be limited to any particular type, shape or structure(s) for doing so.

The proximal connector 125 of the mill 115 is structured to releasably couple to a drill (or rigid/flexible drilling shaft) for driving rotation of the milling bit 130. In the embodiment depicted in the Figures, the proximal connector 125 includes a distally facing stopping surface 255, a set pin hole 280 to receive a set pin (not shown) for releasably coupling the proximal connector 125 to the milling bit 130, and a Hudson fitting 128 for connecting to the drill, though it should be appreciated that other coupling structures may be employed in addition to or in lieu of the Hudson fitting 128, and that various embodiments of the subject disclosure are not intended to be limited to any particular type of coupling structure. It should also be appreciated that the milling bit 130 and/or the proximal connector 125 may be constructed from any materials suitable for milling/cutting implants, such as, for example, stainless steel or tungsten carbide. The milling bit 130 may also be diamond tipped.

With reference to FIGS. 3, 4A, 4B and 6A, the drill guide 120 is generally cylindrical in shape and includes an outside surface 205, a proximal mating end 180 for coupling to the handle coupler 105, a distal engaging end 185 having a shaped cutout 190 extending transversely to a longitudinal axis of the drill guide 120, a longitudinally extending mill receipt bore 195 extending from the mating end 180 to the engaging end 185 and having a diameter approximately equal to but slightly larger than the outer diameter of the milling bit 130, windows 210 extending radially from the mill receipt bore 195 to the outside surface 205, and circumferential screw threads 215 on the outside surface 205 for engaging with the catch cup 127. In the embodiment depicted in the Figures, the cutout 190 is U-shaped for receiving a spine rod, though it should be appreciated that the cutout 190 may exhibit other shapes for mating with other types of implants to be cut/milled by the cutter 100.

The proximal mating end 180 of the drill guide 120 is shaped to be slidably received within the central bore 165 of the handle coupler 105. Guide surfaces 217, 217' provided on the outside surface 205 at the mating end 180 engage respectively with guide surfaces 167, 167' of the handle coupler 105 to ensure proper orientation of the drill guide 120. The screw-like connector 175 of the handle 110 extends through and into the central bore 165 of the handle coupler 105, where it engages frictionally with the outside surface 205 of the mating end 180 of the drill guide 120 to maintain the drill guide 120 firmly within the central bore 165 during operation of the cutter 100.

In the embodiment depicted in the Figures, the windows 210 of the drill guide 120 include four longitudinal sets of windows 210, with each set extending radially from the mill receipt bore 195 to the outside surface 205 at a right angle relative to adjacent longitudinal sets. The windows 210 of two adjacent sets (see FIG. 4A) are formed in part by side surfaces 275 and top surfaces 260 that extend helically in a direction substantially transverse to the helical transport groove 145 of the milling bit 130, whereas the windows 210 of the remaining sets (see FIG. 4B) are formed in part by side surfaces 275 and top surfaces 265 that extend helically in a direction substantially parallel to the helical transport groove 145 of the milling bit 130. The proximal windows 210 of each set are also positioned to coincide longitudinally with the stop 270 of the helical transport groove 145. It should be appreciated, however, that drill guide 120 may be provided with any number of windows 210 in any orientation and of any shape, and that various embodiments of the subject disclosure are not intended to be limited to any particular number, shape or orientation of windows 210.

Figure 2:
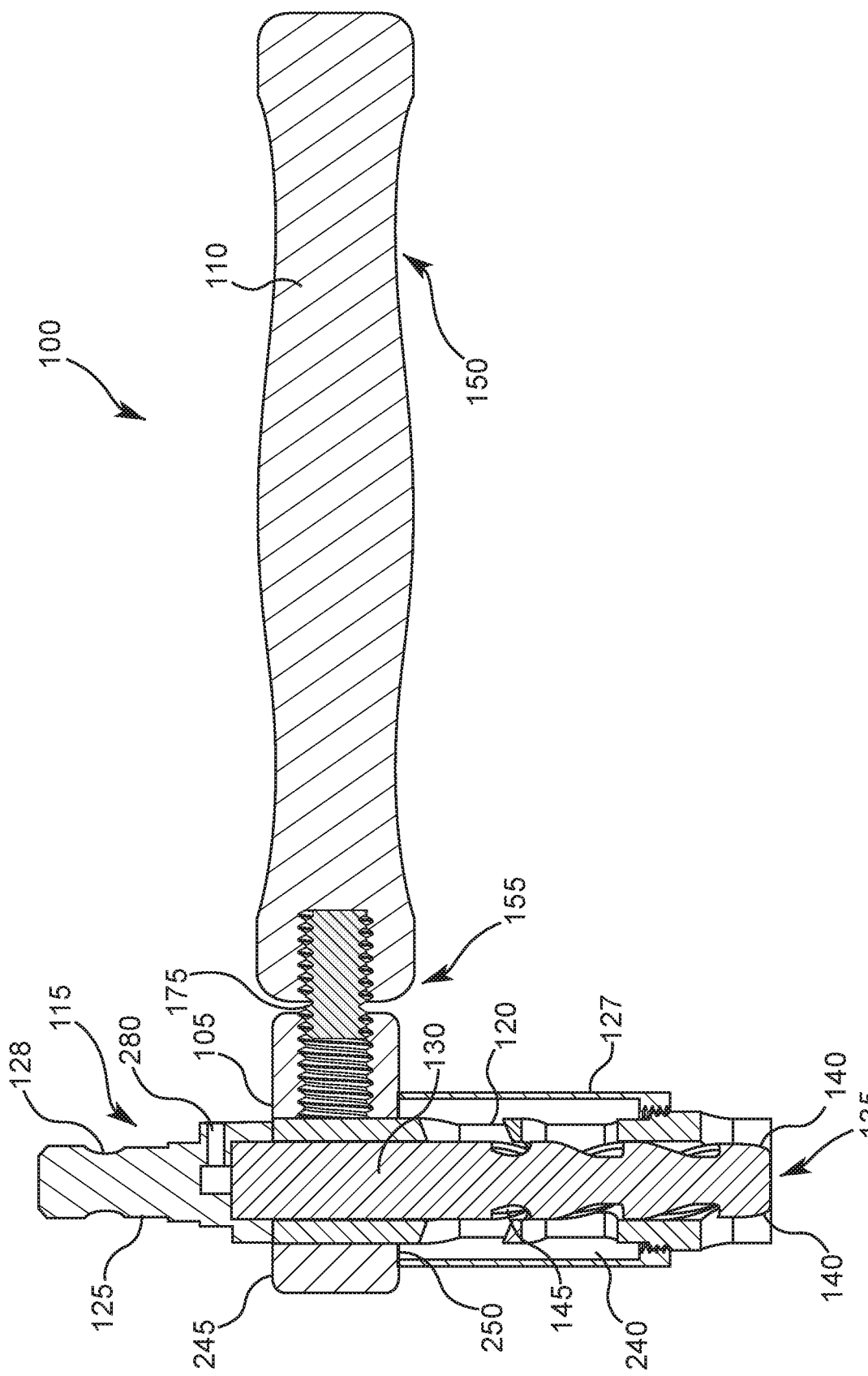
FIG. 2 is a longitudinal-sectional view of the cutter of FIG. 1A.
Figure 7A:
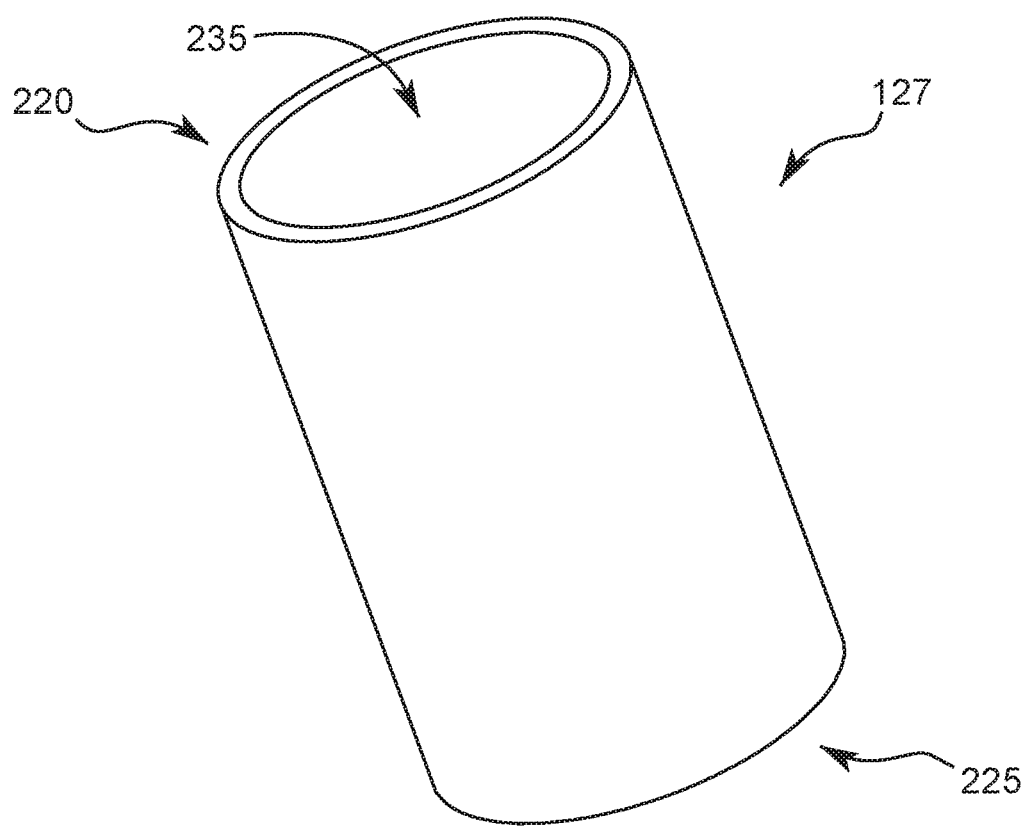
FIG. 7A is a perspective view of a catch cup of the cutter of FIG. 1A.
Figure 7B:
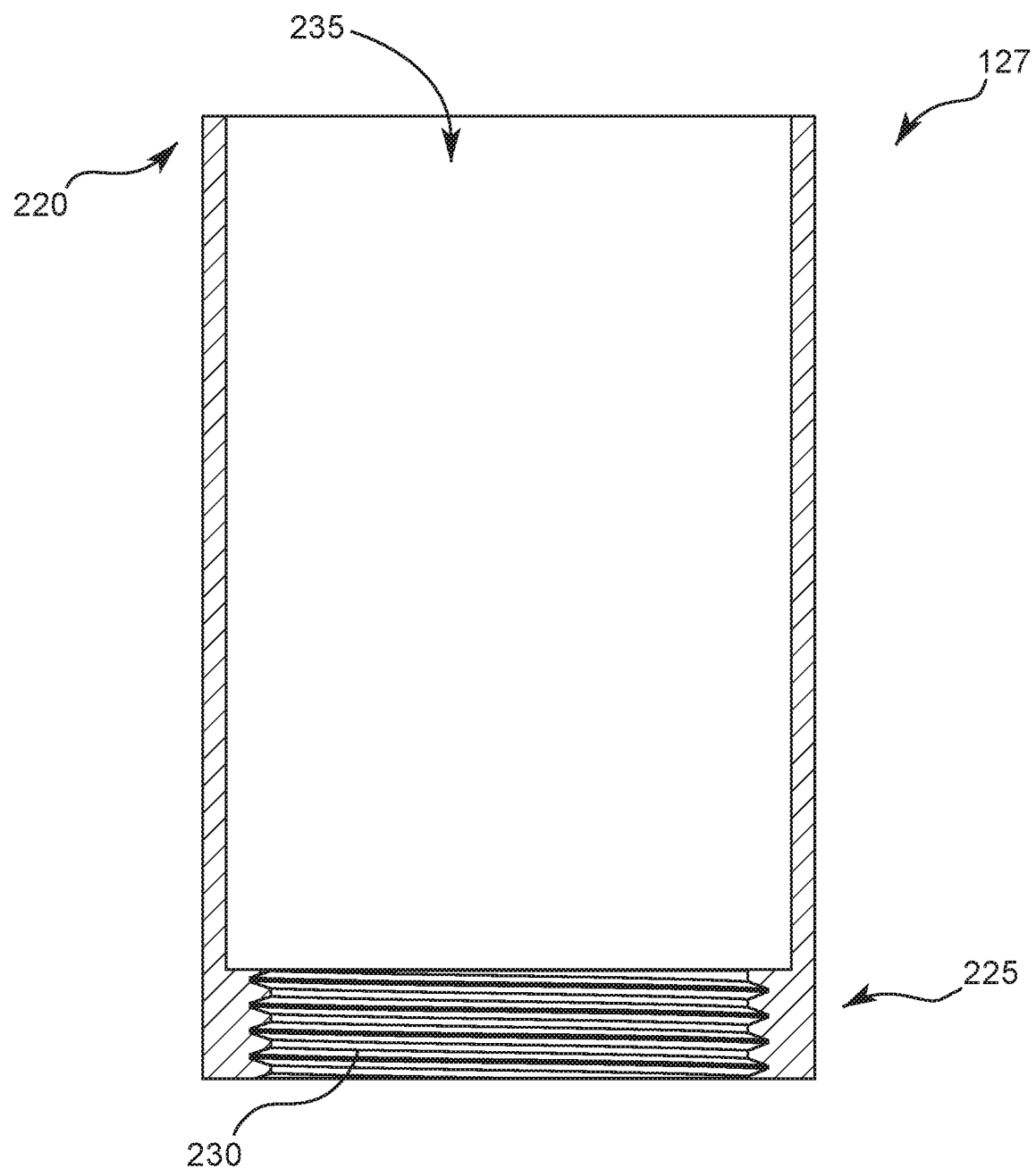
FIG. 7B is a longitudinal-sectional view of a catch cup of the cutter of FIG. 1A.

The catch cup 127 (see FIGS. 7A and 7B) circumscribes the drill guide 120 and includes a proximal end 220 abutting the distal end surface 250 of the handle coupler 105, a distal end 225 provided with inside threads 230 for engaging with the circumferential screw threads 215 of the drill guide 120, and a longitudinal bore 235 having a diameter greater than an outside diameter of the drill guide 120 and extending from the threads 230 at distal end 225 to proximal end 220 of the catch cup 127. As shown best in FIG. 2, when the catch cup 127 is coupled to the drill guide 120 via threads 230, a chip-receipt cavity or receiving cavity 240 is formed to receive chips and other fragments removed from the implant during a cutting/milling operation, in a manner more fully described below. In at least some embodiments, catch cup 127 is constructed from a transparent material (such as a transparent polymer, e.g., plastic) to enable a user to visually confirm receipt of the chips and other fragments within the chip-receipt cavity or receiving cavity 240, though it should be appreciated that other materials may be used (including opaque materials), and that various embodiments of the subject disclosure are not intended to be limited to any particular type(s) of materials for constructing catch cup 127.

To assemble the cutter 100, the drill guide 120 is first inserted proximally into the longitudinal bore 235 of the catch cup 127 until the circumferential screw threads 215 of the drill guide 120 abut the inside threads 230 of the catch cup 127, after which the catch cup 127 is rotated to engage the threads 215, 230 and firmly couple the catch cup 127 to the drill guide 120. The proximal mating end 180 of the drill guide 120 is then inserted proximally into the central bore 165 of the handle coupler 105 until the proximal end 220 of the catch cup 127 contacts the distal end surface 250 of the handle coupler 105, thereby closing off the chip-receipt cavity 240. Next, the screw-like connector 175 of the handle 110 is inserted into the threaded screw bore 170 of the handle coupler 105. The handle 110 is then rotated to advance the connector 175 into the bore 170 until the end of screw-like connector 175 of the handle 110 engages frictionally with the outside surface 205 of the mating end 180, thereby coupling the handle 110 to the handle coupler 105 and rigidly maintaining the drill guide 120 firmly within the central bore 165 of the handle coupler 105.

With the cutter 100 properly assembled, the cutter 100 may then be used to cut/mill an implant, such as a spine rod, implanted within the body of a patient. For this purpose, the user first grips the handle 110 and positions the cutter 100 such that the cutout 190 of the drill guide 120 engages with the implant for properly orienting the cutter 100 thereto and ensuring that the cutter 100 is maintained in a proper position with respect to the implant during operation of the cutter 100. While the user maintains his/her grip on the handle 110, the mill 115 with attached drill (or drill shaft) is then inserted distally through the central bore 165 of the handle coupler 105 and into the mill receipt bore 195 of the drill guide 120 until the distal cutting end 135 of the milling bit 130 engages with the implant.

Figure 6A:
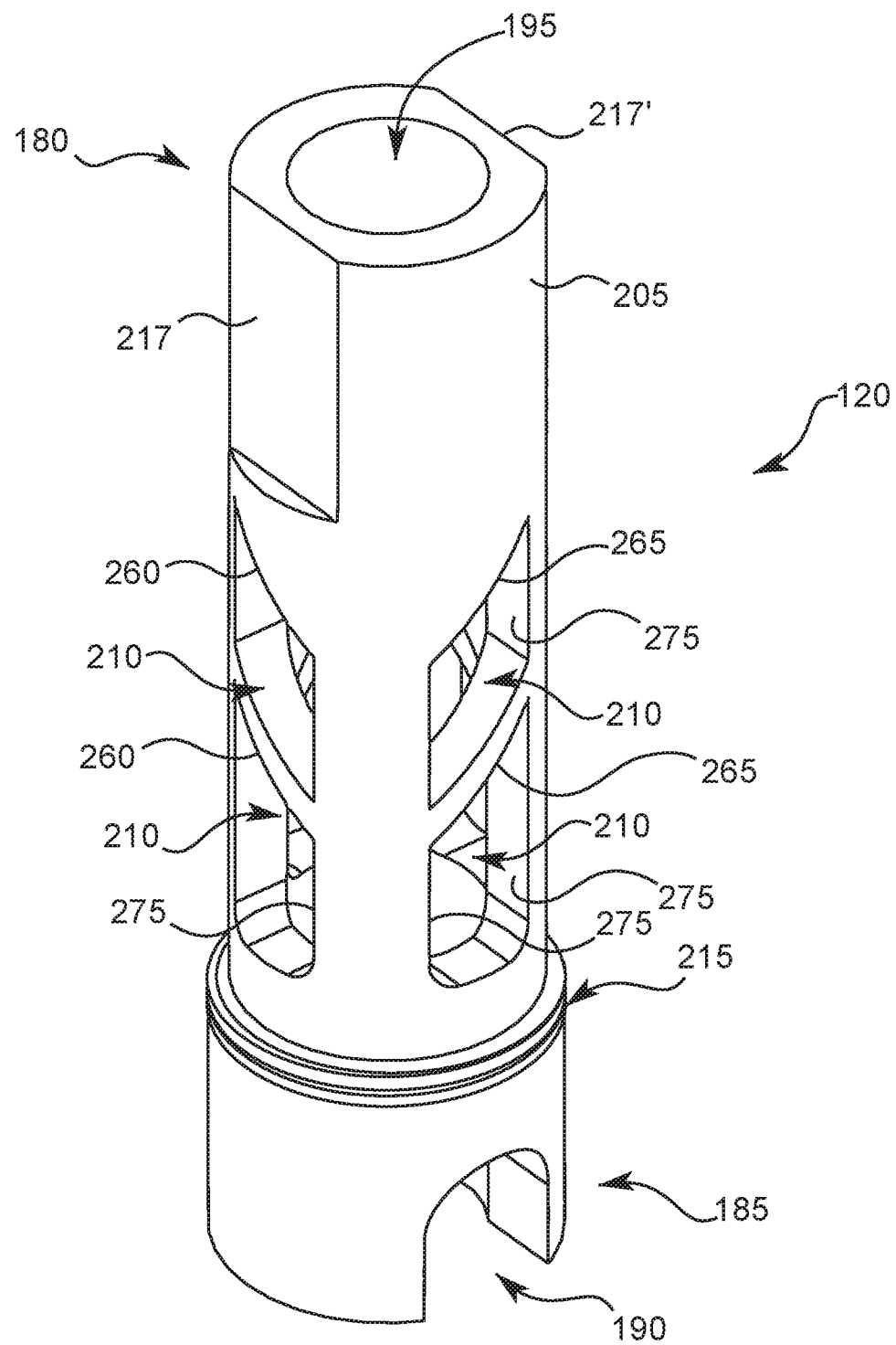
FIG. 6A is a perspective view of a drill guide of the cutter of FIG. 1A.
Figure 6B:
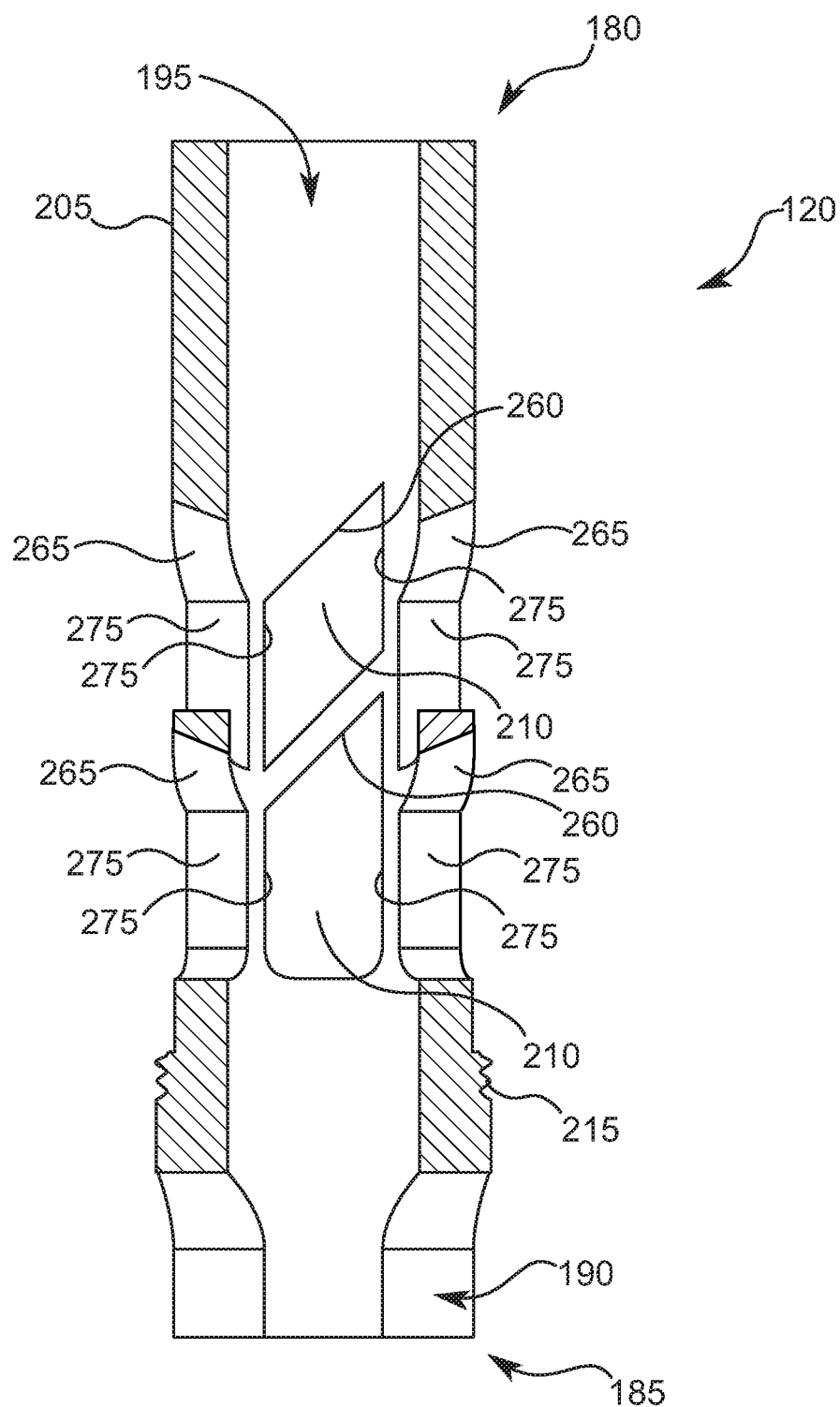
FIG. 6B is a longitudinal-sectional view of an alternative drill guide in accordance with an exemplary embodiment of the subject disclosure.

The drill is then activated and the mill 115 advanced further distally to cut through the implant. As the mill 115 cuts through the implant, chips and other fragments removed from the implant are transported proximally within the drill guide 120 via the helical transport groove 145 of the milling bit 130. As the chips and other fragments move proximally, they engage with top and side surfaces 260, 265, 275 of the windows 210, causing the chips and fragments to exit radially through the windows 210 of the drill guide 120 and into the chip-receipt cavity 240, where they are maintained and prevented from escaping and falling into the body of the patient. Since top surfaces 260, 265 extend in different orientations with respect to the helical transport groove 145 (i.e., top surfaces 260 extend transversely to the groove 145, whereas top surfaces 265 extend parallelly to the groove 145), the probability of chips and fragments catching a surface 260, 265 increases, thereby aiding in removal of the chips from the drill guide 120. With respect to an alternative embodiment of drill guide 120 illustrated in FIG. 6B, removal of chips and fragments may be further aided by edging or "knifing" at least one of top and side surfaces 260, 265, 275, thereby improving the ability of surfaces 260, 265, 275 to catch and transport the chips and fragments into the chip-receipt cavity 240.

The mill 115 is then advanced further distally until the stopping surface 255 of the mill 215 engages with the proximal end surface 245 of the handle coupler 105 to prevent over advancement of the mill 115, at which point the cutting operation is complete. The cutter 100 is then removed from the patient and disassembled to access and discard the removed chips and fragments in the catch cup 127. Any chips and fragments remaining in the transport groove 145 after disassembly may also be removed and discarded.

It will be appreciated by those skilled in the art that changes could be made to the exemplary embodiments described above without departing from the broad inventive concept thereof. It is to be understood, therefore, that this disclosure is not limited to the particular exemplary embodiments disclosed, but it is intended to cover modifications within the spirit and scope of the claims defined herein.

We claim:

1. A cutter for cutting an implant, comprising:
a handle;
a handle coupler for coupling to the handle;
a drill guide distal to the handle coupler for coupling to the handle coupler and including at least one window;
a mill for extending through the handle coupler and the drill guide and disposed to rotate freely therein; and
a catch cup for circumscribing the drill guide to maintain chips of the implant removed by the mill and passed through the at least one window.

2. The cutter of claim 1, wherein the handle is hourglass shaped.

3. The cutter of claim 1, wherein the handle is provided with at least one of stippling, texturing, and a slip-free coating.

4. The cutter of claim 1, wherein the handle coupler includes a central bore and the drill guide includes a proximal mating end structured to be received within the central bore of the handle coupler.

5. The cutter of claim 4, wherein the handle coupler includes at least one first guide surface in communication with the central bore and the proximal mating end of the drill guide includes at least one second guide surface for engaging with the first guide surface of the handle coupler.

6. The cutter of claim 1, wherein the handle coupler includes a threaded screw bore and the handle includes a screw-like connector for engaging with the threaded screw bore to couple the handle to the handle coupler.

7. The cutter of claim 1, wherein the drill guide includes a distal engaging end having a cutout shaped to engage with the implant.

8. The cutter of claim 7, wherein the drill guide includes a distal engaging end having a cutout shaped to engage with a spine rod.

9. The cutter of claim 1, wherein the drill guide includes a mill receipt bore, an outside surface and at least one window extending from the mill receipt bore to the outside surface.

10. The cutter of claim 9, wherein the at least one window includes a top surface oriented substantially transversely to a transport receipt groove.

11. The cutter of claim 9, wherein the at least one window includes a top surface oriented substantially parallelly to a transport receipt groove.

12. The cutter of claim 1, wherein the mill includes a milling bit extending distally to a cutting end and a helical transport groove extending proximally from the cutting end to a stop.

13. The cutter of claim 12, wherein the cutting end is a flat cutting end with rounded edges.

14. The cutter of claim 1, wherein the handle coupler includes a proximal end surface and the mill includes a proximal connector having a distally facing stopping surface for engaging with the proximal end surface to prevent over-advancement of the mill distally into the drill guide.

15. A cutter for cutting an implant, comprising:
a handle;
a handle coupler for coupling to the handle;
a drill guide distal to the handle coupler for coupling to the handle coupler and including at least one window;
a mill for extending through the handle coupler and the drill guide and disposed to rotate freely therein; and
a catch cup circumscribing the drill guide to maintain chips of the implant removed by the mill and passed through the at least one window.

16. The cutter of claim 15, wherein the handle is provided with at least one of stippling, texturing, and a slip-free coating.

17. The cutter of claim 15, wherein the drill guide includes a distal engaging end having a cutout shaped to engage with the implant.

18. The cutter of claim 15, wherein the drill guide includes a mill receipt bore, an outside surface and at least one window extending from the mill receipt bore to the outside surface.

19. A cutter for cutting an implant, comprising:
- a handle coupler having an outside surface, proximal and distal end surfaces extending transversely to the outside surface, a central bore extending longitudinally from the proximal end surface to the distal end surface, and a threaded screw bore extending radially from the central bore to the outside surface of the handle coupler;
- a handle having a proximal gripping end and a distal connecting end having a screw-like connector, the screw-like connector engaging with the threaded screw bore and extending into the central bore of the handle coupler;
- a drill guide having an outside surface, a proximal mating end disposed within the central bore of the handle coupler and maintained therein by the screw-like connector of the handle, a distal engaging end having a cutout shaped to receive the implant, a longitudinally extending mill receipt bore extending from the mating end to the engaging end, a window extending radially from the mill receipt bore to the outside surface of the drill guide, and circumferential screw threads on the outside surface of the drill guide;
- a mill extending through the central bore of the handle coupler and into the mill receipt bore of the drill guide, the mill including a proximal connector having a distally facing stopping surface, a milling bit extending distally from the proximal connector to a distal cutting end, and a helical transport groove extending proximally from the distal cutting end to a stop;
- a catch cup circumscribing the drill guide, the catch cup including a proximal end abutting the distal end surface of the handle coupler, a distal end provided with inside threads engaging with the circumferential screw threads of the drill guide, and a longitudinal bore having a diameter greater than an outside diameter of the drill guide and extending from the inside threads to the proximal end of the catch cup; and
- a receiving cavity formed by the catch cup and drill guide.

20. The cutter of claim 19, wherein the cutout is shaped to receive a spine rod.

* * * * *